United States Patent [19]
Goebel et al.

[11] Patent Number: 4,676,063
[45] Date of Patent: Jun. 30, 1987

[54] MEDIUM-LOAD POWER GENERATING STATION WITH AN INTEGRATED COAL GASIFICATION PLANT

[75] Inventors: Konrad Goebel; Rainer Müller, both of Erlangen; Ulrich Schiffers, Eckental, all of Fed. Rep. of Germany

[73] Assignee: Kraftwerk Union Aktiengesellschaft, Mülheim, Fed. Rep. of Germany

[21] Appl. No.: 829,535

[22] Filed: Feb. 14, 1986

Related U.S. Application Data

[62] Division of Ser. No. 614,469, May 25, 1984, Pat. No. 4,590,760.

[30] Foreign Application Priority Data

May 31, 1983 [DE] Fed. Rep. of Germany ....... 3319732
Jul. 29, 1983 [DE] Fed. Rep. of Germany ....... 3327367

[51] Int. Cl.⁴ ............................. F02C 3/28; F02C 6/10
[52] U.S. Cl. ................................. 60/39.07; 60/39.12
[58] Field of Search ............... 60/39.07, 39.12, 39.465; 518/702, 703

[56] References Cited

U.S. PATENT DOCUMENTS

| | | |
|---|---|---|
| 3,183,666 | 5/1965 | Jackson . |
| 3,849,662 | 11/1974 | Blaskowski et al. ............... 60/39.12 |
| 3,868,817 | 3/1975 | Marion et al. . |
| 3,904,386 | 9/1975 | Graboski et al. ................... 518/703 |
| 4,005,996 | 2/1977 | Hausberger et al. ............... 518/703 |
| 4,404,414 | 9/1983 | Penick et al. ........................ 585/408 |

FOREIGN PATENT DOCUMENTS

| | | |
|---|---|---|
| 0038138 | 10/1981 | European Pat. Off. . |
| 0047596 | 3/1982 | European Pat. Off. . |
| 2807326 | 8/1979 | Fed. Rep. of Germany . |
| 3100751 | 1/1982 | Fed. Rep. of Germany . |
| 1167495 | 10/1969 | United Kingdom . |
| 2075124 | 11/1981 | United Kingdom . |

OTHER PUBLICATIONS

ASME Paper, Title: Novel Gas Turbine Cycles with Coal Gasification, by S. Hamilton, & S. J. Lehman.
Article from Dec. 1979 Combustion—Title: The Integration of Gasification with Combined Cycle Power Plants, by R. W. Foster-Pegg, Westinghouse Electric Corp.

Primary Examiner—Louis J. Casaregola
Attorney, Agent, or Firm—Herbert L. Lerner; Laurence A. Greenberg

[57] ABSTRACT

Medium-load power generating station with an integrated coal gasification plant, a gas turbine power generating station part connected to the coal gasification plant, a steam power generating station part connected to the raw gas heat exchanger plant of the coal gasification plant, a methanol synthesis plant having a plurality of modules connected in parallel to each other, and a purified gas distribution system which connects the methanol synthesis plant to the gas turbine power generating station part and which includes a purified gas continuous flow interim storage plant and is connected on the gas side to the raw gas heat exchanger plant. The methanol synthesis plant is associated, for hydrogen enrichment, to a "cooler-saturator loop" which is connected to the raw gas heat exchanger plant and consists of the saturator, a converting plant, cooler and following gas purification plant. In one mode of operation, a water electrolysis plant is associated with the methanol synthesis plant and its hydrogen line is connected to the methanol synthesis plant, and its oxygen line is connected to the coal gasifier.

4 Claims, 3 Drawing Figures

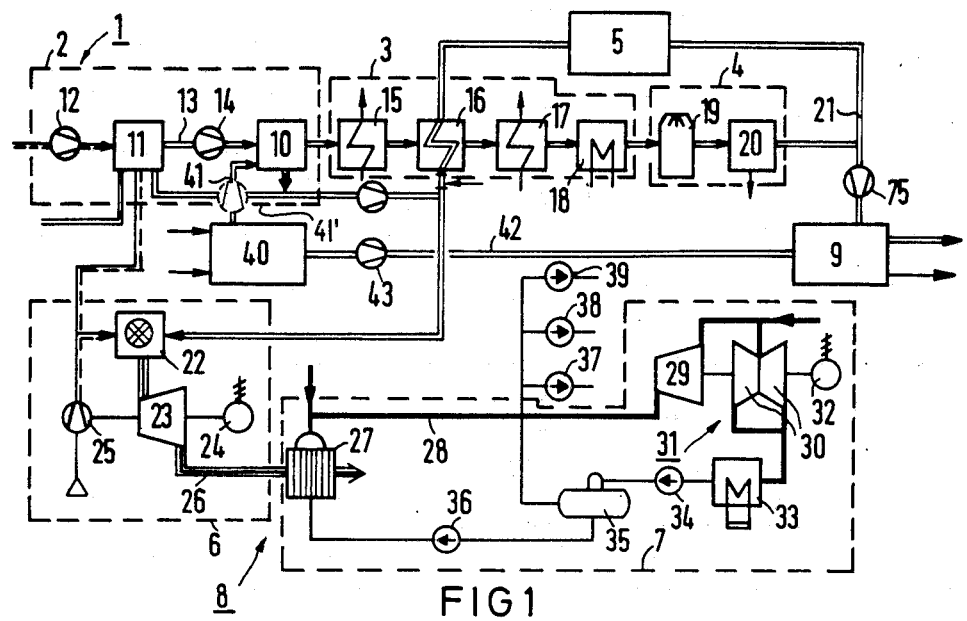
FIG 1
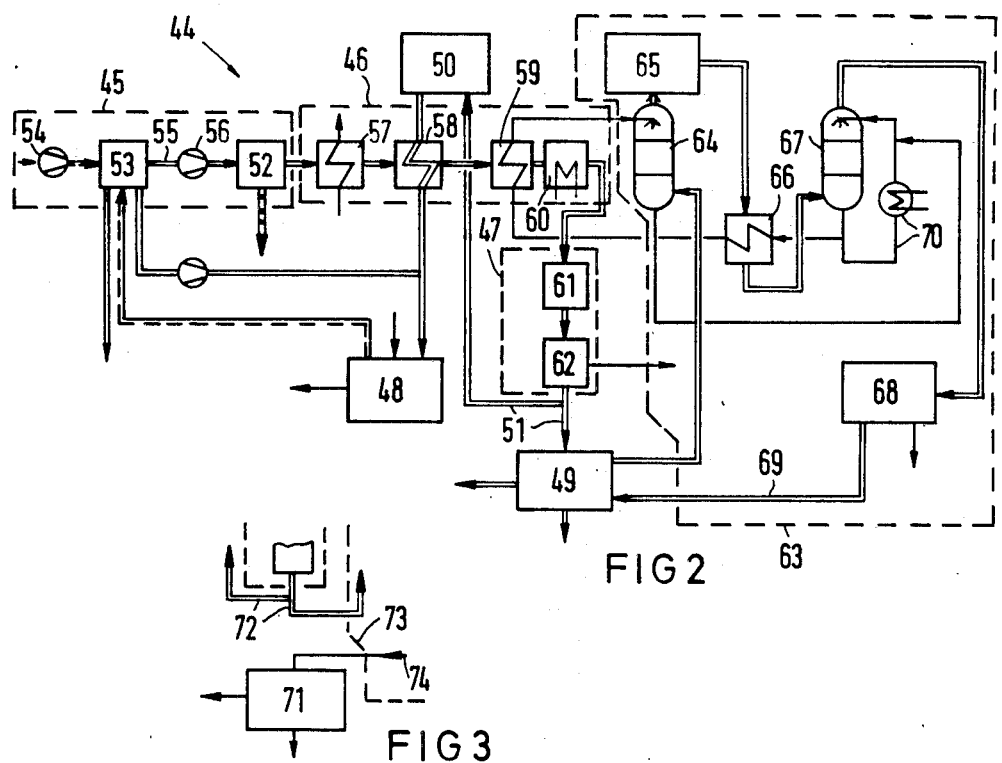
FIG 2
FIG 3

MEDIUM-LOAD POWER GENERATING STATION WITH AN INTEGRATED COAL GASIFICATION PLANT

This is a division of application Ser. No. 614,469, filed May 25, 1984, now U.S. Pat. No. 4,590,760.

CROSS-REFERENCE TO RELATED APPLICATION

The following application, assigned to Kraftwerk Union Aktiengesellschaft, a German corporation, the assignee of the present application is hereby incorporated by reference; Application Ser. No. 614,470, filed for Konrad Goebel, Rainer Muller and Ulrich Schiffers, inventors, on May 25, 1984.

BACKGROUND OF THE INVENTION

1. Field of the Invention

The invention relates to a medium-load power generating station with an integrated coal gasification plant, with a gas turbine generating station part connected to the coal gasification plant with a steam power generating station part connected to the raw gas heat exchanger plant of the coal gasification plant, with a methanol synthesis plant consisting of several parallel-connected modules, and with a purified gas distribution system which connects the methanol synthesis plant to the gas turbine power generating station part and which includes a purified gas continuous-flow interim storage plant and is connected on the gas side to the raw gas heat exchanger plant.

The subject of our related application referred to above, is a medium-load power generating station for generating electric power and methanol, in which a combination gas turbine/steam power generating station and a methanol synthesis plant having a plurality of modules which modules can be added into the stream separately, is connected via a purified gas distribution system, to a coal gasification plant. The waste heat of the raw gas is fed to the steam power generating station part via a raw gas heat exchanger plant and is utilized there. In this medium-load power generating station, the generated electric power can be adapted quickly to the instantaneous power demands of the electric network without the need of employing a further expensive secondary fuel for load peaks and without the need that in the event of a sudden load reduction or even load shedding due to a disturbance, a loss of fuel has to be tolerated. Instead, methanol is produced to a larger degree in this medium-load power generating station at times of reduced demand of electric power and excesses as well as shortfalls of pure gas are buffered by the purified gas continuous flow interim storage plant which is associated with the pure gas distribution system.

Therefore, the relatively more sluggish coal gasification plant can continue to be operated with constant output independently of the prevailing load demands of the electric network. Because the composition of the purified gas flowing toward the methanol synthesis plant is far from the stoichiometric ratio required for the methanol synthesis, the synthesis gas returned in the methanol synthesis reactors of the individual modules must be enriched with hydrogen in times of reduced energy demand to utilize the not completely reacted synthesis gas which can no longer be burned in the combustion chamber of the gas turbine. This hydrogen enrichment could be achieved by external feeding-in of hydrogen.

SUMMARY OF THE INVENTION

An object of the invention is to provide in a medium-load power generating station of the type mentioned at the outset, the hydrogen required for the hydrogen enrichment of the synthesis gas of the methanol synthesis plant from the power generating station itself in a most economical manner.

With the foregoing and other objects in view, there is provided in accordance with the invention a medium-load power generating plant with an integrated coal gasification plant comprising (a) a coal gasification plant for producing a raw hot fuel gas-containing carbon monoxide and hydrogen, (b) a raw gas heat exchanger installation having a first raw gas heat exchanger for indirect heat exchange between the hot raw gas from the coal gasification plant with feedwater to generate steam, (c) a gas purifier for purifying the raw gas, (d) a central purified gas distribution system, (e) a purified gas supply line connected to the raw gas heat exchanger installation and passing into the central purified gas distribution system, (f) a purified gas continuous-flow interim storage plant connected in parallel to the purified gas supply line, (g) a gas turbine power generating plant connected to the coal gasification plant to receive fuel via the purified gas supply line, (h) a methanol synthesis plant having parallel-connected modules for converting CO and $H_2$ into methanol connected to the gas turbine power generating plant via the central purified gas distribution system, the combination therewith of (i) a cooler-saturator loop connected to the raw gas heat exchanger plant for treating a gas therefrom containing carbon monoxide and converting it into a gas richer in hydrogen, comprising a saturator wherein the gas is saturated with moisture, a converter wherein at least part of the carbon monoxide in the gas saturated with moisture is converted to hydrogen and carbon dioxide; a cooler for cooling the products from the converter, a gas purification plant for the removal of carbon dioxide and hydrogen sulfide, if any, from the gas from the cooler, connecting means for passing said purified gas to the methanol synthesis plant for hydrogen enrichment of synthesis gas to be converted into methanol.

In accordance with the invention, there is provided a medium-load power generating plant with an integrated coal gasification plant comprising (a) a coal gasification plant for producing raw hot fuel gas-containing carbon monoxide and hydrogen, (b) a raw gas heat exchanger installation having a first raw gas heat exchanger for indirect heat exchange between the hot raw gas from the coal gasification plant with feedwater to generate steam, (c) a gas purifier for purifying the raw gas, (d) a central purified gas distribution system, (e) a purified gas supply line connected to the raw gas heat exchanger installation and passing into the central purified gas distribution system, (f) a purified gas continuous-flow interim storage plant connected in parallel to the purified gas supply line, (g) a gas turbine power generating plant connected to the coal gasification plant to receive fuel via the purified gas supply line, (h) a methanol synthesis plant having parallel-connected modules for converting CO and $H_2$ into methanol connected to the gas turbine power generating plant via the central purified gas distribution system, the combination therewith of (i) a water electrolysis plant, adapted to utilize electrical power from the combination power station containing the gas turbine power generating station part and the steam power generating station part, to convert water into oxygen and hydrogen, hydrogen connecting means for transferring the hydrogen from the electrolysis plant to the methanol synthesis plant for hydrogen enrichment of synthesis gas to be converted into methanol, and oxygen connecting means for transferring the oxygen from the electrolysis plant to the coal gasifier.

Other features which are considered as characteristic for the invention are set forth in the appended claims.

Although the invention is illustrated and described herein as embodied in a medium-load power generating station with an integrated coal gasification plant, it is nevertheless not intended to be limited to the details shown, since various modifications may be made therein without departing from the spirit of the invention and within the scope and range of equivalents of the claims.

BRIEF DESCRIPTION OF THE DRAWINGS

The invention, however, together with the additional objects and advantages thereof will be best understood from the following description when read in conjunction with the accompanying drawings, in which:

FIG. 1 is a schematic presentation of a medium-load power generating station with an integrated coal gasification plant and a water electrolysis plant associated with the methanol synthesis plant, FIG. 2 is a different medium-load power generating station with an integrated coal gasification plant and a so-called "cooler-saturator loop" associated with the methanol synthesis plant, and FIG. 3 is a variant for connecting the methanol synthesis plant of FIG. 2 is the so-called "cooler-saturator loop".

DETAILED DESCRIPTION OF THE INVENTION

The invention relates to a medium-load power generating station with an integrated coal gasification plant with a gas turbine power generating station part connected to the coal gasification plant, with a steam power generating station part connected to the raw gas heat exchanger plant of the coal gasification plant and with a methanol synthesis plant. In such a medium-load power generating station, more methanol is generated in times of reduced power demand. The remaining synthesis gas is now no longer burned in the gas turbine, has a composition far short of that desired and the objective is to bring the composition closer to the stoichiometric ratio required for the methanol synthesis. To this end, the methanol synthesis plant is associated for the purpose of hydrogen enrichment, with a so-called cooler-saturator loop which is connected to the raw gas heat exchanger plant and includes a saturator, a converting plant, coolers and a gas purification plant connected thereto. Furthermore, a water electrolysis plant can also be associated with the methanol synthesis plant with a hydrogen line from the electrolysis plant connected via a compressor to the methanol synthesis plant. Fossil fuels are suitable for use with a medium-load power generating station according to the invention.

In a medium-load power generating station of the type mentioned at the outset, the methanol synthesis plant, according to the invention, is therefore associated for the hydrogen enrichment with a so-called "cooler-saturator loop" which is connected to the raw gas heat exchanger plant and consists of saturator, conversion plant, cooler and a following gas purification plant. In such a cooler-saturator loop hydrogen and carbon dioxide are generated by introduction of steam into the synthesis gas and subsequent conversion of the synthesis gas/steam mixture. After separating the carbon dioxide, the remaining synthesis gas, enriched with hydrogen, is returned to the methanol synthesis plant.

As an alternative, a water electrolysis plant in which water is converted to hydrogen and oxygen by electrolysis, the hydrogen is connected by a hydrogen line to the methanol synthesis plant and the oxygen by an oxygen line to the coal gasification plant, thereby associating the water electrolysis plant with the medium-load power generating station and with the methanol synthesis plant. In such an arrangement, the electric power generated in excess at times of reduced power demands, can be utilized in the water electrolysis plant for generating hydrogen and oxygen gases. The hydrogen can be used immediately for the enrichment of the synthesis gas of the methanol synthesis plant. The simultaneously generated oxygen can be fed to the coal gasifier. The oxygen there substitutes for a part of the oxygen which would otherwise be supplied by the air separation plant, reducing the output of the latter and thereby saving energy.

Further details of the invention will be explained with the aid of two embodiment examples shown in the drawings.

In the presentation of FIG. 1, the superimposed assemblies of the medium-load power generating station 1 are framed by dashed lines. These are coal gasifier 2, a raw gas heat exchanger plant 3, a gas purification plant 4, a central purified gas distribution system 5 with an integrated pressurizer and storage plant (not shown here for the sake of clarity), a combination power generating station 8 consisting of a gas turbine power generating station part 6 and a steam power generating station part 7, and a methanol synthesis plant 9. The coal gasification plant 2 includes a coal gasifier 10, and air separation plant 11 with at least one additional air compressor 12 preceding the air separation plant, and a further oxygen gas compressor 14 which is arranged in the oxygen line 13 leading from the air separation plant 11 to the coal gasifier 10. The raw gas heat exchanger plant 3 arranged in the gas stream from the coal gasifier 10 includes a first heat exchanger 15 for generating high-pressure steam, a second raw gas/purified gas heat exchanger 16 and a third heat exchanger 17 for generating low-pressure steam. Finally, a control cooler 18 is provided in the raw-gas heat exchanger plant 3. The gas purification plant 4 following the raw gas heat exchanger plant includes a raw gas scrubber 19 as well as a hydrogen sulfide absorption and sulfur extraction plant 20. To the purified gas line 21 leaving the hydrogen sulfide absorption and sulfur extraction plant 20 are connected the purified gas distribution system 5, the methanol synthesis plant 9 and, via the raw gas/purified gas heat exchanger 16, the gas turbine power generating plant part 6.

The gas turbine power generating station part 6 includes a combustion chamber 22, a gas turbine 23 and one generator 24 and one air compressor 25 driven by the gas turbine 23.

The exhaust gas line 26 of the gas turbine 23 is connected to a waste heat boiler 27. Its steam line 28 is connected to the high-pressure part 29 of a steam turbine 31 consisting of a high-pressure part 29 and a low-pressure part 30. A generator 32 is coupled to the steam turbine 31. The low-pressure part 30 of the steam turbine 31 is followed by a condenser 33, a condensate pump 34, a feedwater tank 35 as well as several feedwater pumps 36, 37, 38, 39. The combustion chamber 22 of the gas turbine as well as the air separation plant 11 of the coal gasification plant 2 are connected to the air compressor 25 driven by the gas turbine 23. A water electrolysis plant 40, wherein water is converted to oxygen and hydrogen, is associated with the coal gasification plant. The oxygen line 41 of the electrolysis plant 40 is connected in parallel to the oxygen line 13 of the air separation plant 11 to the coal gasifier 10. If it is desired to operate the coal gasifier 10 at the same pressure as the methanol synthesi reactor, a compressor 41' shown in dashed lines in interposed in the oxygen line 41. In such event sufficient pressure may be generated by compressor 41' and compressor 25 may not be needed. The hydrogen line 42 of the water electrolysis plant 40 is connected via a hydrogen gas compressor 43 to the methanol synthesis plant 9.

In the operation of the medium-load power generating station 1, the air separation plant 11 is supplied with air by the air compressor 25 driven by the gas turbine 23 as well as by the supplemental air compressor 12. The oxygen of the air separation plant is forced into the coal gasifier 10 by the gas compressor 14. Coal is gasified with oxygen and fed-in process steam in the coal gasifier 10 to form raw gas. The hot raw gas discharged from gasifier 10 at a temperature of 800° to 1600° C. gives off its heat in the heat exchanger plant 3, being utilized in part to generate high-pressure steam in the first heat exchanger 15. In the second raw gas/purified gas heat exchanger 16, the purified gas flowing toward the combustion chamber 22 of the gas turbine power generating plant part 6 is preheated by the raw gas. In the third heat exchanger 17, additional heat from the raw gas is utilized to generate low-pressure steam which can be fed to the low pressure part 30 of the steam turbine 31 or can be used as process steam. The control cooler 18 cools the raw gas to a defined temperature before it enters the raw gas scrubber 19. The pressure maintenance which takes place in the purified gas line 21 leaving the gas purification plant 4 is accomplished via the purified gas distribution system 5 with an integrated purified gas continuous flow interim storage plant.

The methanol synthesis plant 9, which is subdivided into several modules which can separately be cut-in or cut-out of operation, remains switched-on in the operation of the medium load power generating station 1 at nominal load with at least one module which operates in continuous flow operation. At so-called low-load times when less electric power is given off to the network, the gas turbine power generating station part 6 is cut back first. The excess purified gas is consumed by running the modules of the methanol synthesis plant 9 which happened to be in operation at higher capacity, or by adding further modules. Thus, the coal gasification plant 2 can be continued to be operated in the optimum range for gasification of coal. The water electrolysis plant 40 can be set in operation with part of the excess steam while the output of the gas turbine power generating station part is reduced at the same time. The hydrogen produced by electrolysis can be fed through line 42 into the methanol synthesis plant 9 by means of the compressor 43. Thereby, the composition of the pure gas fed into the methanol synthesis plant or of the synthesis gas recirculating in the methanol synthesis plant is brought closer to the stoichiometric ratio required for the methanol synthesis. The oxygen produced at the same time in the water electrolysis plant 40 is fed to the coal gasifier 10. This oxygen substitutes for part of the oxygen from the air separation plant 11. As a result, the output of the air separation plant 11 can be reduced. In this manner, the quantity of methanol generated in times of reduced power demand can be increased by modifying the synthesis gas composition normally going to the methanol synthesis plant to a composition closer to the stoichiometric ratio by the addition of hydrogen generated by excess electric power. By this procedure the entire amount of active constituents, namely carbon monoxide and hydrogen in the purified gas generated at nominal load of the coal gasifier 10 which is not needed by the gas turbine power generating station part 6 is completely converted into methanol.

A further increase in methanol quantity is produced if additionally, hydrocarbon containing gas from an external source (not shown) is cracked to form synthesis gas and this gas is fed into the methanol synthesis plant. In this case, the entire electric power of the network can be fed to the water electrolysis plant 40 in an extreme case of complete separation of the medium/low power generation station 1 from this network. Since in this mode of operation of the medium/low power generating station, only a small amount of the purified gas generated by the coal gasifier is available for methanol synthesis, there is inadequate hydrogen to effect complete reaction of the carbon monoxide in the purified gas to methanol by methanol synthesis, and this hydrogen is available from the hydrocarbon containing gas fed-in from the external source to substantially complete the methanol synthesis. The coal gasification plant 2 is continued to be operated at nominal load regardless of whether the combination power generating station 8 consisting of a gas turbine part 6 and a steam generating station part 7 is continued to be operated at nominal load at times of reduced power demands or whether its output is reduced in such times. The purified gas produced in excess and/or at the same time, synthesis gas from the cracking of additional hydrocarbon containing gas is converted into methanol.

The medium-load power generating station 44 of the embodiment example shown in FIG. 2 consists of a coal gasification plant 45, a raw gas heat exchanger plant 46, a gas purification plant 47, a combination power generating station 48 including a gas turbine power generating station part and a steam power generating station part, a methanol synthesis plant 49 and a central purified/gas distribution system 50 with a purified gas continuous-flow interim storage plant (not shown here for the sake of clarity) connected in parallel to the purified gas line 51. The coal gasification plant 45 includes a coal gasifier 52, and air separation plant 53, a supplemental air compressor 54 preceding the air separation plant 53, and an oxygen gas compressor 56 arranged in the oxygen line 55 to the coal gasifier 52. Also, the raw gas heat exchanger plant 46 associated with the raw gas stream issuing from the coal gasifier 52 includes a heat exchanger 57 for generating steam, a raw gas/purified gas heat exchanger 58, a heat exchanger 59 for generating hot water, and control cooler 60. The gas purification plant 47 following the raw gas heat exchanger plant 46 includes a raw gas scrubber 61 and a hydrogen sulfide absorption and sulfur extraction plant 62.

The purified gas line 51 leaving the gas purification plant 47 is connected, similar to the embodiment example of FIG. 1, to the central purified gas distribution system 50, the methanol synthesis plant 49 and, via the purified gas/raw gas heat exchanger 58, to the combination power generating station 48. The latter is designed as shown in detail in the embodiment example of FIG. 1.

In a modification of the embodiment example of FIG. 1, a so-called "cooler-saturator loop" 63 is connected to the methanol synthesis plant 49. The loop includes a saturator 64, a converter 65, a heat exchanger 66, a cooler 67 and a gas purification plant 68. The synthesis gas enriched in the cooler-saturator loop with hydrogen is returned via a recirculation line 69 to the methanol synthesis plant 49 and is fed to the synthesis reactor (not shown for clarity) of the methanol synthesis plant.

In the operation of the medium-load power generating station 44 raw gas is generated in the coal gasifier 52 with the oxygen of the air separation plant 53 and with steam in a manner similar to that described in connection with embodiment example of FIG. 1. Raw gas issuing from coal gasifier 52 is cooled in the following raw gas heat exchanger plant 46 and is purified in the gas purification plant 47. The combination power generated station 48 including a gas turbine power generating station part and a steam power generating station part is operated by burning in the gas turbine the purified gas from the gas distribution system 50 after first preheating the purfied gas in the raw gas/purified gas heat exchanger 58. Also, the high-pressure steam generated in the first heat exchanger 57 of the raw gas heat exchanger plant 46 is fed to the steam turbine of the steam power generating station part. The synthesis gas partially reacted in the modules of the methanol synthesis plant 49, but which gas contains unreacted carbon monoxide, is conducted into the saturator 64 with steam by means of hot water which is taken from the third heat exchanger 59 of the raw gas heat exchanger plant 46, thereby saturating the synthesis with moisture. The mixed gas obtained in this manner is converted in the following converting plant 65 by reaction of the carbon monoxide with water to give carbon dioxide and hydrogen. The exhaust gas of the converting plant 65 is cooled in a first heat exchanger 66, where the cooling water warmed up in this exchanger is fed for further heating into the third heat exchanger 59 of the raw gas heat exchanger plant 46. The thus precooled exhaust gas of the converting plant 65 is further cooled in a cooler 67 connected to the cooler loop 70 and the cooled exhaust gas from cooler 67 introduced into the gas purification plant 68. In this gas purification plant, the carbon dioxide is washed out and the remaining gas enriched with hydrogen is returned as synthesis gas via the recirculation line 69 to the methanol synthesis plant 49. There, it is fed to a synthesis reactor which is in operation.

If desired, the exhaust gas of the converting plant may be treated in a gas separation plant to obtain a fraction rich in hydrogen by liquification of the less volatile gaseous constituents. Also, the purified gas flowing initially into the methanol synthesis plant may be enriched with hydrogen via the cooler-saturator loop instead of making synthesis gas from the synthesis reactor of the methanol synthesis plant, in order that the synthesis gas approach a stoichiometric ratio for the methanol generation.

This synthesis gas enriched with hydrogen could then be fed to the methanol synthesis plant and recirculated there through the individual synthesis reactors until it is completely reacted to methanol, except, of course, for the inert gas residues. The connection of the methanol synthesis plant 71 for this type of pre-enrichment of the purified gas with hydrogen is shown in the embodiment example of FIG. 3. It is seen here that the purified gas line 72 is first fed to the otherwise unchanged cooler-saturator loop 73 and only the exhaust gas which is enriched with hydrogen and freed of carbon dioxide is fed to the converting plant behind the gas purification plant via the recirculating line 74 into the methanol synthesis plant 71.

The output of the gas turbine can also be reduced or the turbine can be switched off at times when less power is fed into the electric network. The purified gas which under these conditions is available in larger quantity, can be converted via the methanol synthesis plant into methanol while the synthesis gas is enriched with hydrogen. The heat produced in larger quantity in the third heat exchanger 59 of the raw gas heat exchanger plant 46 can be utilized for further saturation of the pure gas and in some circumstances, for the additional decomposition of externally introduced hydrocarbon containing gas. Due to the increase of the synthesis gas production, more methanol can be produced.

There is claimed:

1. A medium-load power generating plant with an integrated coal gasification plant comprising
   (a) a coal gasification plant for producing raw hot fuel gas-containing carbon monoxide and hydrogen,
   (b) a raw gas heat exchanger installation having a first raw gas heat exchanger for indirect heat exchange between the hot raw gas from the coal gasification plant with feedwater to generate steam,
   (c) a gas purifier for purifying the raw gas,
   (d) a central purified gas distribution system,
   (e) a purified gas supply line connected to the raw gas heat exchanger installation and passing into the central purified gas distribution system,
   (f) a purified gas continuous-flow interim storage plant connected in parallel to the purified gas supply line,
   (g) a gas turbine power generating plant connected to the coal gasification plant to receive fuel via the purified gas supply line,
   (h) a methanol synthesis plant having parallel-connected modules each with a reactor for converting CO and $H_2$ into methanol connected to the gas turbine power generating plant via the central purified gas distribution system, the combination therewith of
   (i) a water electrolysis plant, adapted to utilize electrical power from the combination power station containing the gas turbine power generating station part and the steam power generating station part, to convert water into oxygen and hydrogen, hydrogen connecting means for transferring the hydrogen from the electrolysis plant to the methanol synthesis plant for hydrogen enrichment of synthesis gas to be converted into methanol, and oxygen connecting means for transferring the oxygen from the electrolysis plant to the coal gasifier.

2. Medium-load power generating station according to claim 1, wherein the coal gasifier operates at the same pressure as the water electrolysis plant and wherein one compressor is interposed in the purified gas feedline leading to the methanol synthesis plant and another compressor is interposed in the hydrogen line from the electrolysis plant to the methanol synthesis plant.

3. Medium-load power generating station according to claim 1, wherein the coal gasifier operates at the same pressure as the methanol synthesis reactor, and wherein a compressor is interposed in the oxygen line between the water electrolysis plant and the coal gasifier and another compressor interposed in the hydrogen line to the methanol synthesis reactor.

4. Medium-load power generating station according to claim 1, wherein the hydrogen line from the electrolysis plant is connected to the purified gas line leading to a module of the methanol synthesis plant.

* * * * *